(12) United States Patent
Chen et al.

(10) Patent No.: US 8,361,483 B2
(45) Date of Patent: Jan. 29, 2013

(54) EPINECIDIN-1 AS A VACCINE ADJUVANT FOR ENHANCING IMMUNE RESPONSES

(75) Inventors: Jyh-Yih Chen, Ilan (TW); Chang-Jer Wu, Taipei (TW)

(73) Assignee: Academia Sinica, Taipei (TW)

( * ) Notice: Subject to any disclaimer, the term of this patent is extended or adjusted under 35 U.S.C. 154(b) by 47 days.

(21) Appl. No.: 13/070,197

(22) Filed: Mar. 23, 2011

(65) Prior Publication Data

US 2012/0244186 A1    Sep. 27, 2012

(51) Int. Cl.
*A61K 45/00* (2006.01)
*A61K 39/193* (2006.01)
*A61K 39/12* (2006.01)
*A61K 39/00* (2006.01)

(52) U.S. Cl. ............... 424/278.1; 424/218.1; 424/204.1; 424/184.1

(58) Field of Classification Search .......................... None
See application file for complete search history.

(56) References Cited

PUBLICATIONS

Huang HN, Pan CY, Rajanbabu V, Chan YL, Wu CJ, Chen JY. Modulation of immune responses by the antimicrobial peptide, epinecidin (Epi)-1, and establishment of an Epi-1-based inactivated vaccine. Biomaterials. 2011. 32:3627-36.*

Luiza Deszcz, Regina Cencic, Carla Sousa, Ernst Kuechler, and Tim Skern. An Antiviral Peptide Inhibitor That Is Active against Picornavirus 2A Proteinases but Not Cellular CaspasesJ Virol. 2006. 80(19): 9619-9627.*

Wang YD et al. Antiviral activity by fish antimicrobial peptides of epinecidin-1 and hepcidin 1-5 against nervous necrosis virus in medaka. Peptides. Jun. 2010;31(6):1026-33. Epub May 7, 2010.*

* cited by examiner

*Primary Examiner* — Zachariah Lucas
*Assistant Examiner* — Nianxiang Zou
(74) *Attorney, Agent, or Firm* — Hsiu-Ming Saunders; Intellectual Property Connections, Inc.

(57) ABSTRACT

A method of enhancing a mammalian immune response to a virus is disclosed. The method comprises administering a composition comprising an effective amount of epinecidin (Epi)-1 and the virus to a mammal, wherein the virus has envelope protein and is infectious to the mammal. A vaccine kit and a method for preventing Japanese encephalitis virus (JEV) infection are also disclosed.

19 Claims, 8 Drawing Sheets

SEQUENCE LISTING

```
<160> NUMBER OF SEQ ID NOS: 29

<210> SEQ ID NO 1
<211> LENGTH: 21
<212> TYPE: PRT
<213> ORGANISM: Epinephelus coioides

<400> SEQUENCE: 1

Gly Phe Ile Phe His Ile Ile Lys Gly Leu Phe His Ala Gly Lys Met
1               5                   10                  15

Ile His Gly Leu Val
            20

<210> SEQ ID NO 2
<211> LENGTH: 22
<212> TYPE: DNA
<213> ORGANISM: Artificial Sequence
<220> FEATURE:
<223> OTHER INFORMATION: Stat1 sense

<400> SEQUENCE: 2
tgtctagtgt tatgagttgg tt                                              22

<210> SEQ ID NO 3
<211> LENGTH: 21
<212> TYPE: DNA
<213> ORGANISM: Artificial Sequence
<220> FEATURE:
<223> OTHER INFORMATION: Stat1 antisense

<400> SEQUENCE: 3
```

```
cttctggtgt ccatacattc a                                              21

<210> SEQ ID NO 4
<211> LENGTH: 18
<212> TYPE: DNA
<213> ORGANISM: Artificial Sequence
<220> FEATURE:
<223> OTHER INFORMATION: IL2 sense

<400> SEQUENCE: 4
tctgaggaga tggatagc                                                  18

<210> SEQ ID NO 5
<211> LENGTH: 18
<212> TYPE: DNA
<213> ORGANISM: Artificial Sequence
<220> FEATURE:
<223> OTHER INFORMATION: IL2 antisense

<400> SEQUENCE: 5
tgttgtaagc aggaggta                                                  18

<210> SEQ ID NO 6
<211> LENGTH: 18
<212> TYPE: DNA
<213> ORGANISM: Artificial Sequence
<220> FEATURE:
<223> OTHER INFORMATION: Tlr1 sense

<400> SEQUENCE: 6
atgaaggctc tgataact                                                  18

<210> SEQ ID NO 7
<211> LENGTH: 18
<212> TYPE: DNA
<213> ORGANISM: Artificial Sequence
<220> FEATURE:
<223> OTHER INFORMATION: Tlr1 antisense

<400> SEQUENCE: 7
cttgtggtaa ttggtagg                                                  18

<210> SEQ ID NO 8
<211> LENGTH: 19
<212> TYPE: DNA
<213> ORGANISM: Artificial Sequence
<220> FEATURE:
<223> OTHER INFORMATION: IL1f6 sense

<400> SEQUENCE: 8
tgttcaggat cttagtagt                                                 19

<210> SEQ ID NO 9
<211> LENGTH: 18
<212> TYPE: DNA
<213> ORGANISM: Artificial Sequence
<220> FEATURE:
<223> OTHER INFORMATION: IL1f6 antisense

<400> SEQUENCE: 9
agcaaggtaa tagtgact                                                  18

<210> SEQ ID NO 10
<211> LENGTH: 18
<212> TYPE: DNA
<213> ORGANISM: Artificial Sequence
<220> FEATURE:
```

<223> OTHER INFORMATION: Ifnb1 sense

<400> SEQUENCE: 10
tacagggcgg acttcaag                                                 18

<210> SEQ ID NO 11
<211> LENGTH: 18
<212> TYPE: DNA
<213> ORGANISM: Artificial Sequence
<220> FEATURE:
<223> OTHER INFORMATION: Ifnb1 antisense

<400> SEQUENCE: 11
ctcattccac ccagtgct                                                 18

<210> SEQ ID NO 12
<211> LENGTH: 19
<212> TYPE: DNA
<213> ORGANISM: Artificial Sequence
<220> FEATURE:
<223> OTHER INFORMATION: Gapdh sense

<400> SEQUENCE: 12
acaatgaata cggctacag                                                19

<210> SEQ ID NO 13
<211> LENGTH: 18
<212> TYPE: DNA
<213> ORGANISM: Artificial Sequence
<220> FEATURE:
<223> OTHER INFORMATION: Gapdh antisense

<400> SEQUENCE: 13
ggtccagggt ttcttact                                                 18

<210> SEQ ID NO 14
<211> LENGTH: 18
<212> TYPE: DNA
<213> ORGANISM: Artificial Sequence
<220> FEATURE:
<223> OTHER INFORMATION: Stat2 sense

<400> SEQUENCE: 14
aaggcacaac agcatagt                                                 18

<210> SEQ ID NO 15
<211> LENGTH: 19
<212> TYPE: DNA
<213> ORGANISM: Artificial Sequence
<220> FEATURE:
<223> OTHER INFORMATION: Stat2 antisense

<400> SEQUENCE: 15
agatggtaca gcagagaac                                                19

<210> SEQ ID NO 16
<211> LENGTH: 18
<212> TYPE: DNA
<213> ORGANISM: Artificial Sequence
<220> FEATURE:
<223> OTHER INFORMATION: Nfkb1 sense

<400> SEQUENCE: 16
atttgctttg tgttgtta                                                 18

<210> SEQ ID NO 17

-continued

```
<211> LENGTH: 18
<212> TYPE: DNA
<213> ORGANISM: Artificial Sequence
<220> FEATURE:
<223> OTHER INFORMATION: Nfkb1 antisense

<400> SEQUENCE: 17
ttacagtaga tggctaga                                                 18

<210> SEQ ID NO 18
<211> LENGTH: 18
<212> TYPE: DNA
<213> ORGANISM: Artificial Sequence
<220> FEATURE:
<223> OTHER INFORMATION: Ifna7 sense

<400> SEQUENCE: 18
cttcctcaga ctcataac                                                 18

<210> SEQ ID NO 19
<211> LENGTH: 19
<212> TYPE: DNA
<213> ORGANISM: Artificial Sequence
<220> FEATURE:
<223> OTHER INFORMATION: Ifna7 antisense

<400> SEQUENCE: 19
atctaaagtc ctttctgtc                                                19

<210> SEQ ID NO 20
<211> LENGTH: 18
<212> TYPE: DNA
<213> ORGANISM: Artificial Sequence
<220> FEATURE:
<223> OTHER INFORMATION: Myd88 sense

<400> SEQUENCE: 20
ttcactgctt gatgttga                                                 18

<210> SEQ ID NO 21
<211> LENGTH: 20
<212> TYPE: DNA
<213> ORGANISM: Artificial Sequence
<220> FEATURE:
<223> OTHER INFORMATION: Myd88 antisense

<400> SEQUENCE: 21
gcccttcttt tctttattga                                               20

<210> SEQ ID NO 22
<211> LENGTH: 21
<212> TYPE: DNA
<213> ORGANISM: Artificial Sequence
<220> FEATURE:
<223> OTHER INFORMATION: Ifng sense

<400> SEQUENCE: 22
cacacctgat tactaccttc t                                             21

<210> SEQ ID NO 23
<211> LENGTH: 20
<212> TYPE: DNA
<213> ORGANISM: Artificial Sequence
<220> FEATURE:
<223> OTHER INFORMATION: Ifng antisense

<400> SEQUENCE: 23
```

```
cctcaaactt ggcaatactc                                                    20

<210> SEQ ID NO 24
<211> LENGTH: 23
<212> TYPE: DNA
<213> ORGANISM: Artificial Sequence
<220> FEATURE:
<223> OTHER INFORMATION: IL4 sense

<400> SEQUENCE: 24
ttagcatctc ttgataaact taa                                                23

<210> SEQ ID NO 25
<211> LENGTH: 18
<212> TYPE: DNA
<213> ORGANISM: Artificial Sequence
<220> FEATURE:
<223> OTHER INFORMATION: IL4 antisense

<400> SEQUENCE: 25
aaatgccgat gatctctc                                                      18

<210> SEQ ID NO 26
<211> LENGTH: 21
<212> TYPE: DNA
<213> ORGANISM: Artificial Sequence
<220> FEATURE:
<223> OTHER INFORMATION: IL7r sense

<400> SEQUENCE: 26
gaccttgcta cacatcttca g                                                  21

<210> SEQ ID NO 27
<211> LENGTH: 23
<212> TYPE: DNA
<213> ORGANISM: Artificial Sequence
<220> FEATURE:
<223> OTHER INFORMATION: IL7r antisense

<400> SEQUENCE: 27
attcaccaca tccttctatc ttc                                                23

<210> SEQ ID NO 28
<211> LENGTH: 19
<212> TYPE: DNA
<213> ORGANISM: Artificial Sequence
<220> FEATURE:
<223> OTHER INFORMATION: Mx1 sense

<400> SEQUENCE: 28
cctgccatcg ctgtcattg                                                     19

<210> SEQ ID NO 29
<211> LENGTH: 19
<212> TYPE: DNA
<213> ORGANISM: Artificial Sequence
<220> FEATURE:
<223> OTHER INFORMATION: Mx1 antisense

<400> SEQUENCE: 29
tgcctctcca ctcctctcc                                                     19
```

EPINECIDIN-1 AS A VACCINE ADJUVANT FOR ENHANCING IMMUNE RESPONSES

FIELD OF THE INVENTION

The present invention relates generally to antimicrobial peptides, and more specifically to epinecidin-1.

BACKGROUND OF THE INVENTION

Prophylactic vaccinations are hailed as a miracle of modern medicine, the efficacy of a given vaccine, however, varies with the formulated antigenic context it contains. Unlike small-molecule drugs, vaccines are made of diverse materials, including proteins, polysaccharides, DNA, viruses, virus-like particles, irradiated live cells, synthetic peptides, and attenuated live organisms (viruses, bacteria, or parasites). In general, vaccines composed of antigenic proteins or their subunits are less immunogenic than 'traditional vaccines' (inactivated pathogens), so that they are often fortified with adjuvants such as aluminum, oligonucleotides (CpG DNA sequences), oil emulsions (MF59), and saponin-based mixtures (QS-21 and ISCOMATRIX). The clinical use of some adjuvants, for example aluminum, has however raised some safety concerns. Safer and more-effective adjuvants are constantly being searched for in contemporary vaccine development.

To date, three kinds of JEV vaccines exist, all of which possess some adverse effects as reported from time to time. For example, an imbalance in the immune system can be provoked when formalin-inactivated vaccines are used against measles or respiratory syncytial virus. Incomplete inactivation by formaldehyde was condemned for being incapable of controlling outbreaks of Venezuelan equine encephalitis and foot and mouth disease. Hence, suitable and effective inactivating agents are urgently needed to avoid repeating such unfortunate incidences.

Antimicrobial peptides (AMPs) are a family of short cationic peptides synthesized and released by a wide variety of organisms. Recently, a synthetic adjuvant termed IC31 (composed of the antimicrobial peptide, KLKL5KLK, and deoxy-inosine/deoxy-cytosine (ODN1a)) was revealed to be able to satisfactorily induce antigen-specific Th1 cellular and humoral immune responses. Plus, a DNA vaccine in conjunction with the synthetic KLKL5KLK AMP was also reported to have good efficacy against *Mycobacterium tuberculosis* infections. Although several hundred AMPs have been identified, only a few of their roles in host immunity have been studied.

SUMMARY OF THE INVENTION

Epi-1, a peptide from fish, is non-toxic to cells and animals. It can cause lysis and destruction of virus particles. Epi-1 can replace formaldehyde in traditional methods for preparing vaccines. Epi-1 is much safer, more time-efficient and more effective than formalin in inactivating viruses. An additional advantage for substituting Epi-1 for formalin in manufacturing vaccine is that Epi-1 is also an effective vaccine adjuvant that can enhance a mammalian immune responses to virus infection.

In one aspect, the invention relates to a method of enhancing a mammalian immune response to a virus, comprising administering a composition comprising an effective amount of epinecidin (Epi)-1 and the virus to a mammal in need thereof; and thereby enhancing the immune responses of the mammal against the virus, wherein the virus has envelope protein and is infectious to the mammal.

In another aspect, the invention relates to a method of preventing Japanese encephalitis virus (JEV) infection in a mammal in need thereof, comprising enhancing the mammal's immune response to the JEV by administering a composition comprising an effective amount of epinecidin (Epi)-1 and the JEV according to the method as aforementioned. The method of preventing Japanese encephalitis virus (JEV) infection may further comprise causing enhanced production of anti-envelope protein antibody in the mammal.

In another aspect, the invention relates to a method of enhancing a mammalian immune response to a virus, comprising co-administering an effective amount of Epi and the virus to a mammal in need thereof, and thereby enhancing the mammal's immune response against the virus, wherein the virus has envelope protein and is infectious to the mammal.

In another aspect, the invention relates to a method of preventing Japanese encephalitis virus (JEV) infection in a mammal in need thereof, comprising enhancing the mammal's immune response to the JEV by co-administering an effective amount of Epi and the virus to the mammal according to the method as aforementioned.

Further in another aspect, the invention relates to a method of enhancing an animal's immune response to an infectious virus, comprising administering a composition comprising an effective amount of epinecidin (Epi)-1 and the infectious virus to an animal in need thereof, and thereby enhancing the animal's immune response against the virus, wherein the virus is not a nervous necrosis virus.

Yet in another aspect, the invention relates to a vaccine kit comprising: (a) a composition comprising an effective amount of epinecidin (Epi)-1 and a Japanese encephalitis virus (JEV); and (b) an insert containing instructions on the method of preventing Japanese encephalitis virus (JEV) infection according to a method as aforementioned.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIG. 2 shows Epinecidin (Epi)-1 activates neutralizing antibodies against Japanese encephalitis virus (JEV). C3H/HeN mice were injected with 200 μg/ml of Epi-1, JEV, or JEV co-treated with different doses (50, 100, and 200 μg/ml) of Epi-1, then serum samples were collected at 4 (a) and 21 days (b) post-injection. Serum was assessed for the presence of an anti-JEV envelope (E) protein-specific antibody in an ELISA plate, and the result was converted to units/ml in relation to a serially diluted control antibody. Sera collected from 50× the 50% lethal dose ($LD_{50}$) of JEV alone (JEV), and JEV with 50 (E50), 100 (E100), and 200 (E200) μg/ml were included in the experiment. $*p<0.05$. Error bars, s.d. (n=4~7).

FIG. 7 shows epinecidin (Epi)-1-based Japanese encephalitis virus (JEV)-inactivated vaccine induced specific anti-JEV antibodies in neonate mice. (a) C3H/HeN neonate mice received three doses of immunization with formaldehyde-JEV- or Epi-1-JEV-inactivated vaccines at 7 (primary immunization), 14 (booster 1), and 28 (booster 2) days of age. Serum samples were subjected to an ELISA based on an anti-JEV-E neutralization assay. $*p<0.05$. Error bars, s.d. (n=4~7) (b) JEV-E neutralization efficiency of immunized mice at 4 days after viral challenge. The control group was treated with PBS. $*p<0.05$. Error bars, s.d. (n=4~7).

DETAILED DESCRIPTION OF THE INVENTION

Definitions

Figure 1:
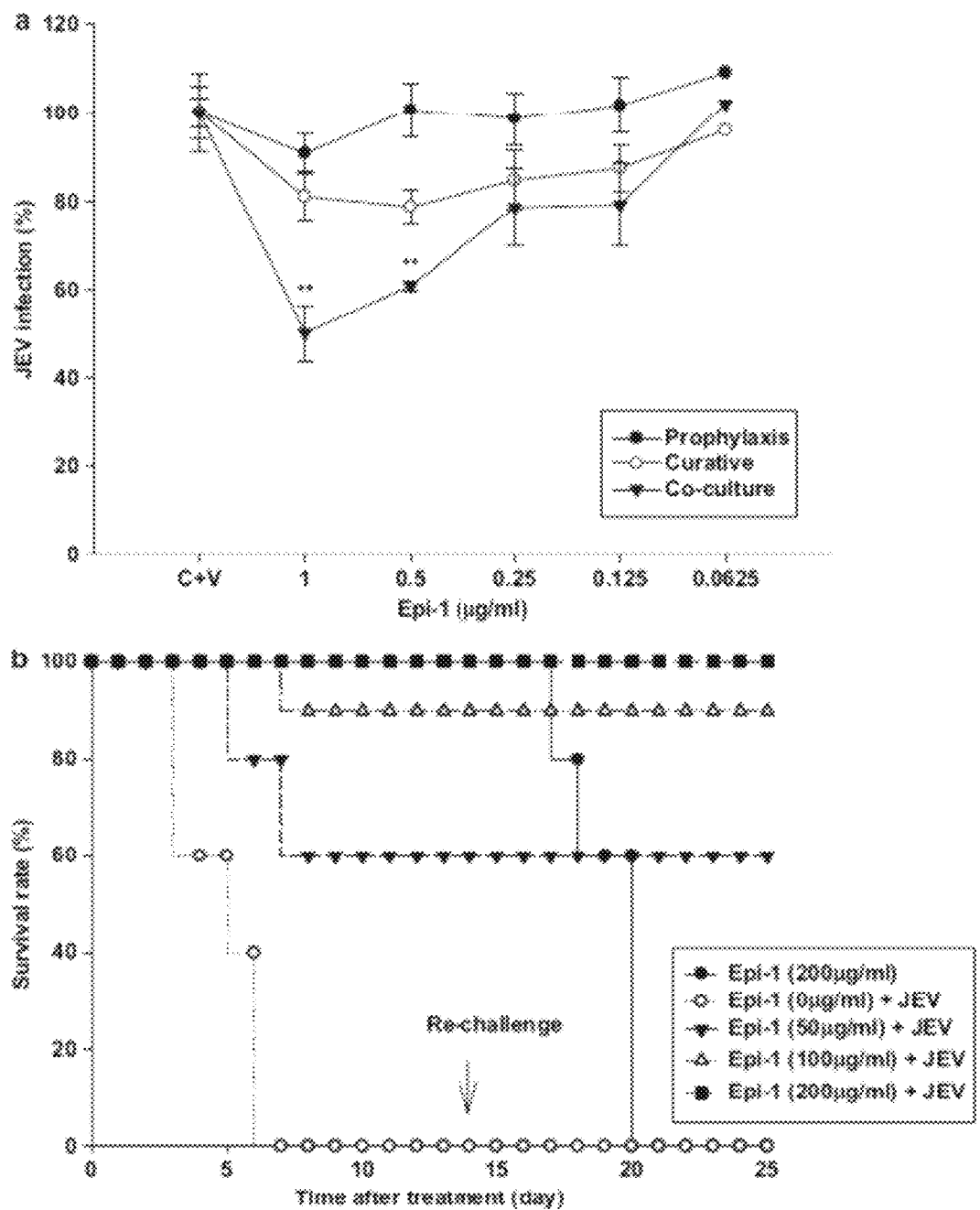
FIG. 1 shows Epinecidin (Epi)-1 controls Japanese encephalitis virus (JEV) infection. (a) Different concentrations of Epi-1 were used to treat BHK-21 cells with JEV at a multiplicity of infection (MOI) of 0.1 by three methods. For prophylaxis treatment, Epi-1 was given first, and cells were infected with JEV 1 h later. For co-treatment, Epi-1 and JEV were given at the same time, while Epi-1 was injected 1 h later than JEV for curative treatment. The percentage of cells infected by JEV was calculated by measuring cell inhibition. Cell inhibition values of samples infected with 0.1 MOI JEV alone (C+V) were converted to 100%, and other treatment values (0.1 MOI JEV+Epi-1) were normalized to that. *$p<0.05$. Error bars, SEM. (n=4~7) (b) Survival curves of C3H/HeN mice treated with JEV and Epi-1. Adult mice were injected with 200 µg/ml of Epi-1, JEV, or JEV co-treated with different doses (50, 100, and 200 µg/ml) of Epi-1. Surviving mice were re-challenged with JEV on the 14th day. Survival of treated mice was monitored on a daily basis for up to 25 days. (n=10~13).

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The term "adjuvant" shall generally mean a substance enhancing the immune response to an antigen.

The term "enhancing an immune response" or "an enhanced response" to a virus means a greater immune response in the presence of the adjuvant, Epi, than without the adjuvant, Epi.

Likewise, "enhanced production," "enhanced secretion," and "enhanced gene expression" shall generally mean greater production, greater secretion and greater gene expression, respectively, in the presence of the adjuvant, Epi, than without the adjuvant, Epi.

An antibody titer is a measurement of how much antibody an organism has produced that recognizes a particular epitope, expressed as the greatest dilution ratio (or its reciprocal) that still gives a positive result. ELISA is a common means of determining antibody titers.

To establish an Epi-1 based inactivated vaccines, Japanese encephalitis virus (JEV) was used as a model for studying virus infections. The Japanese encephalitis virus (JEV), a member of the family Flaviviridae, causes deadly encephalitis in humans and animals. JEV is composed of three virion proteins, capsid (C), premembrane/membrane (prM/M), and envelope (E) proteins. The E-protein was found to be the most protective antigen that elicits a considerable number of neutralizing antibodies.

Epinecidin-1 (Epi-1; SEQ ID NO: 1), derived from grouper (*Epinephelus coioides*), was characterized as being an AMP, and also possesses other properties such as antitumor, antimicrobial, and antiviral activities. It was investigated whether this host-friendly AMP could possibly be substituted for formalin in JEV inactivation in addition to being an adjuvant. The inventors characterized Epi-1 function by JEV infection, evaluated the performance of Epi-1 that applied an Epi-1-based JEV-inactivated vaccine against JEV infection in mice, elucidated the function of Epi-1 mixed with virus in mice after JEV infection, and demonstrated the immune-related genes responses by microarray and real-time polymerase chain reaction (PCR) experiments. Moreover, isotypes of immunoglobulin G (IgG) were also determined in Epi-1-induced immunity against JEV infection.

In one aspect, the invention relates to a method of enhancing a mammalian immune response to a virus, comprising administering a composition comprising an effective amount of epinecidin (Epi)-1 and the virus to a mammal in need thereof, and thereby enhancing the immune responses of the mammal against the virus, wherein the virus has envelope protein and is infectious to the mammal.

In one embodiment of the invention, the aforementioned method further comprises causing enhanced production of anti-envelope protein antibody in the mammal.

In another embodiment of the invention, the aforementioned method further comprises causing enhanced activation of T-helper cells in the mammal.

In another embodiment of the invention, the aforementioned method further comprises causing enhanced secretion of IL-4 in the mammal.

In another embodiment of the invention, the virus is a Japanese encephalitis virus (JEV).

In another embodiment of the invention, the composition comprises a unit dose of at least 200 µg of EPi.

In another embodiment of the invention, the aforementioned method further comprises causing enhanced production of neutralizing antibody against the virus in the mammal.

In another embodiment of the invention, the aforementioned method further comprises causing enhanced expression of an immune-responsive gene, wherein the immune-responsive gene is chosen from B-cell CLL/lymphoma 2 (Bcl-2), interleukin 4 (IL-4) and suppressor of cytokine signaling 3 (SOCS3).

In another embodiment of the invention, the administering step is performed at least 3 times at a specified time interval.

In another aspect, the invention relates to a method of preventing Japanese encephalitis virus (JEV) infection in a mammal in need thereof, comprising enhancing the mammal's immune response to the JEV by administering a composition comprising an effective amount of epinecidin (Epi)-1 and the JEV according to the method as aforementioned. The method of preventing Japanese encephalitis virus (JEV) infection may further comprise causing enhanced production of anti-envelope protein antibody in the mammal.

In another aspect, the invention relates to a method of enhancing a mammalian immune response to a virus, comprising co-administering an effective amount of Epi and the virus to a mammal in need thereof, and thereby enhancing the mammal's immune response against the virus, wherein the virus has envelope protein and is infectious to the mammal.

In one embodiment of the invention, the co-administering step is performed at least 3 times at a specified time interval.

In another aspect, the invention relates to a method of preventing Japanese encephalitis virus (JEV) infection in a mammal in need thereof, comprising enhancing the mammal's immune response to the JEV by co-administering an effective amount of Epi and the virus to the mammal according to the method as aforementioned.

Further in another aspect, the invention relates to a method of enhancing an animal's immune response to an infectious virus, comprising administering a composition comprising an effective amount of epinecidin (Epi)-1 and the infectious virus to an animal in need thereof, and thereby enhancing the animal's immune response against the virus, wherein the virus is not a nervous necrosis virus.

Yet in another aspect, the invention relates to a vaccine kit comprising: (a) a composition comprising an effective amount of epinecidin (Epi)-1 and a Japanese encephalitis virus (JEV); and (b) an insert containing instructions on the method of preventing Japanese encephalitis virus (JEV) infection according to a method as aforementioned.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Materials and Methods

Mice, Cells, and the Virus

Baby hamster kidney (BHK)-21 cells were purchased and maintained as per American Type Culture Collection (ATCC no. CCL10, Manassas, Va., USA) instructions. Female C3H/HeN mice, purchased from the National Laboratory Animal Breeding and Research Center (Taiwan) and BioLASCO (Taipei, Taiwan), were housed at the Laboratory Animal Facility, National Taiwan Ocean University NTOU; Keelung, Taiwan). Mice were maintained in pathogen-free sterile isolators according to institutional guidelines, and all food, water, caging, and bedding were sterilized before use. All procedures were approved by the Animal Care and Use Committee of NTOU. The 50% lethal dose ($LD_{50}$) of JEV in female C3H/HeN mice was determined. The Beijing-1 JEV strain was maintained in suckling mouse brains as previously described.

Cell Proliferation Assay

BHK-21 cells in 48-well plates were assayed with CellTiter 96 Aqueous One Solution (Promega, Madison, Wis., USA) following the vendor's instructions. Epi-1 was administered together with Japanese encephalitis virus (JEV) as co-treatment; Epi-1 was administered 24 h prior to (prophylaxis) or after (curative) the JEV inoculation. After blank value subtraction, the percentage survival against control cells was calculated. The percentage of JEV infection or cell inhibition was obtained by subtracting the cell viability percentage from 100. The epinecidin-1 sequence is GFIFHIIKGLFHAGKMIHGLV (SEQ ID NO: 1) (Wang et al "Inactivation of nervous necrosis virus infecting grouper (*Epinephelus coioides*) by epinecidin-1 and hepcidin 1-5 antimicrobial peptides, and down-regulation of Mx2 and Mx3 gene expressions" Fish & Shellfish Immunology 28 (2010) 113-120, which is herein incorporated by reference in its entirety).

Viral Challenge and Epi-1 Treatments

Six-week-old adult C3H/HeN mice were randomly divided into five groups of 10 mice each. Individuals in each group of mice were intraperitoneally (i.p.) injected with 100 μl of PBS containing 50× the $LD_{50}$ of JEV in the presence or absence of 50, 100, or 200 μg/ml Epi-1 or phosphate-buffered saline (PBS). After 14 days, a re-challenge was carried out on surviving mice with 50× the $LD_{50}$ of JEV. Mouse survival and activity were monitored on a daily basis for up to 25 days after the primary injection. For serological studies, serum was collected on days 4, 7, and 21 after treatment. A similar approach was followed to test immunized mice.

Anti-JEV-E Protein Antibody Assay

Serum was collected by tail bleeding, and an anti E-protein antibody assay was conducted as described previously with some modifications. Briefly, 10-fold-diluted standard serum was serially diluted 2-fold. JEV-antigen-coated 96-well plates were treated with blocking buffer, and 50 μl of standard serum dilutions was loaded into each well in triplicate for 1 h at 37° C. After aspiration and washing steps, a 1:1000-diluted goat horseradish peroxidase (HRP)-conjugated goat anti-mouse IgG antibody (ICN/Cappel, Aurora, Ohio, USA) was added to each well for 2 h at 37° C. Next, aliquots were aspirated and washed, and 50 μl of 10 ml O-phenylenediamine dihydrochloride (OPD) (Sigma-Aldrich, St. Louis, Mo., USA) was added. The reaction mixture was incubated in the dark for 30 min at room temperature, and the peroxidase activity was measured at an absorbance of $OD_{495}$. From the standard curve between the serial dilution and absorbance values, the absorbance values reached a plateau referred to as the $OD_{max}$. Then the reciprocal of the dilution extent corresponding to ½ of the $OD_{max}$ was referred to as one unit (U) of anti-JEV-E neutralization. Readings of unknown samples were compared with standard serum, and results were expressed as arbitrary units/ml. A biotin-conjugated rat anti-mouse IgG1 or IgG2a (Pharmingen, San Diego, Calif., USA) detector was used to measure the respective IgG isotypes. Then Avidin HRP was added, and color development was recorded.

Plaque Reduction Neutralization Test (PRNT)

Neutralization tests were carried out using BHK-21 cells with the 50% plaque-reduction technique. A 2-fold dilution of sera with PBS (containing 5% fetal bovine serum (FBS) (Invitrogen, San Diego, Calif., USA)) was incubated at 56° C. for 30 min to inactivate the complement. The solution was then mixed with an equal volume of JEV solution in minimum essential medium (MEM; Invitrogen, San Diego, Calif., USA) containing 5% FBS to yield approximately 1000 plaque-forming units (pfu) of a virus solution (virus/ml). The virus-antibody mixtures were incubated at 4° C. overnight, and then added to triplicate wells of 6-well plates. Each well contained a confluent monolayer of BHK-21 cells, which was incubated at 37° C. for 1 h with gentle shaking every 15 min. The wells were then overlaid with 2 ml of 1.5% agarose (SeaPlaque, FMC, USA) in MEM containing 2% FBS. The plates were incubated for 3 days at 37° C. in a 5% $CO_2$ atmosphere. Cells then were fixed with formalin and stained with 1% crystal violet. Plaque numbers were counted. Neutralizing antibody titers were calculated as the reciprocal of the highest dilution factor, which resulted in a 50% reduction in the numbers of plaques compared to the control virus (that was mixed with normal sera from naïve C3H/HeN mice of the same age).

Cytokine ELISA

Cytokines levels were quantified by an ELISA according to the manufacturer's instructions. IL-2, IL-4, IL-5, IL-6, IL-10, IL-12, MCP-1, TNF-α, and IFN-γ, were assessed using paired antibodies from the mouse cytokine ELISA set, BD OptEIA™ (BD Bioscience, San Diego, Calif., USA). Briefly, ELISA plates (Nunc, UK) were coated with capture antibody overnight at 4° C. Wells were washed and blocked with 1% bovine serum albumin (BSA) in PBS for 1 h at room temperature. A sample or standard was added for 2 h at 37° C., and bound cytokines were detected using a biotinylated anti-cytokine antibody, avidin HRP, and tetramethylbenzidine. Color development was stopped with 2 M $H_2SO_4$, and optical densities were read at 450 nm. The concentration of the cytokine was determined from the standard curve.

Microarray Analysis

RNA was extracted from different treatment groups of mouse brain with the Trizol reagent, and two independent replicates were separated for each sample. All of these treated groups were compared to the PBS control. Isolated total RNA was quantified on a Nanodrop ND-1000 spectrophotometer (Wilmington, Del., USA). cRNA from 1.5 μg of total RNA from each sample was amplified and labeled with cyanine-3 (Cy3) according to the 1-color labeling protocol of a low=RNA input linear amplification kit (Agilent Technologies, Santa Clara, Calif., USA). The resulting Cy3-cRNA samples were purified using RNeasy mini kits (Qiagen, Valencia, Calif., USA), then the cRNA concentration and dye incorporation were quantified using a Nanodrop spectrophotometer in order to determine the labeling efficiency. cRNA samples were hybridized to 4×44-k mouse oligo microarrays using Agilent reagents and protocols. After hybridization, the arrays were washed, scanned, and analyzed following Agilent protocols. All data were entered into Agilent GeneSpring GX7 (Agilent Technologies) and Pathway Studio software (Ariadne Genomics, Rockville, Md., USA) for analysis and data mining. Genes considered to be significantly regulated were based on an average expression level change of ≧2-fold (average ratio of biological duplicates of ≧2 or ≦0.5). The gene list was converted to a log 2 ratio, and analyzed using Pathway Studio 6.2 software. Genes which showed a direct relationship with the entities based on protein expression, transcription, and regulation were mapped using Adriane ontology. Gene symbols were color-coded red for up-regulated and green for down-regulated conditions and are shown in a graphical representation.

Isolation of Messenger (m)RNA and Real-Time PCR

Total RNA was isolated from brain tissues and purified using a Qiagen RNeasy kit (Qiagen). Reverse transcription into complementary c-DNA was performed with iScript cDNA Synthesis Kits (BIO-RAD) according to the manufacturer's recommendations. A real-time PCR analysis was used to analyze the gene expressions using primers listed in Table 2, according to the manufacturer's instructions. The IQ™ SYBR® Green Supermix (BIO-RAD) and specific primer pairs were used for selected genes, and the primer pair for GAPDH was used as the reference gene. A quantitative PCR; was performed according to the following conditions: 40 cycles of 1 min at 95° C., 30 s at 55° C., and 1 min at 72° C. Using 0.5 μl of cDNA, 2×SYBR Green PCR Supermix, and 500 nM of the forward and reverse primers, the threshold cycle number (Ct) was calculated with BIO-RAD software. Relative transcript quantities were calculated using the ΔCt method with GAPDH as the reference gene which was amplified from the same samples. ΔCt is the difference in the threshold cycles of mRNA for selected genes relative to those of GAPDH mRNA. The real-time PCR was performed in triplicate for each experimental group.

Immunofluorescence Study

Tissue sections on slides were fixed with 3.7% paraformaldehyde (PFA), and washed three times in PBS. The fixed sample was permeabilized with a 0.2% Triton X-100 solution for 15 min at 37° C., and washed with PBS. Blocking was performed using 5% normal bovine serum in PBS for 30 min at 37° C. Then the section was incubated with an anti-JEV-E primary antibody overnight at 4° C., and rinsed three times with PBS for 5 min. Sections were next treated with a goat anti-mouse-conjugated FITC secondary antibody (Cappel, Organon Teknika, Veedijk, Belgium) for 45 min at room temperature (RT). After washing three times with PBS, the stained brain tissues were observed under a fluorescence microscope (BX-51, Olympus, Tokyo, Japan) equipped with a digital camera.

Western Blotting

Proteins were extracted from mouse brain samples as previously described with some modifications. Mouse brain regions were homogenized in urea buffer consisting of 125 mM Tris-HCl (pH 6.8), 2.2% sodium dodecylsulfate (SDS), 5% β-mercaptoethanol, 10% glycerol, 8 M urea, and a protease inhibitor (Boehringer Mannheim, Mannheim, Germany). Then the mixture was centrifuged, and the insoluble materials were removed. After quantification, 10 μg of denatured proteins was separated by 10% SDS-polyacrylamide gel electrophoresis (PAGE), and transferred to a nitrocellulose membrane. The membrane was blocked with 3% milk powder and 2% BSA in TBS/Tween-20 at RT for 1 h, and incubated with a 1:1000-diluted anti-JEV-E primary antibody, followed by a goat anti-mouse HRP-conjugated secondary antibody (Amersham, Little Chalfont; UK). The antibody was detected by a chemiluminescent Western blot detection system (Amersham) over x-ray film. Data were analyzed by UVP Vision Works Software (vers. 5.5.3) (UVP, Upland, Calif., USA).

Immunization of Neonate Mice by Inactivated Vaccines

One-week-old C3H/HeN neonate mice were separated into four groups of 13 mice each. Each group was separately i.p.-injected with $1.5 \times 10^7$ pfu of JEV alone, formalin-inactivated JEV vaccine (10 μg/mice), Epi-1-JEV-inactivated vaccine (10 μg/mice), or PBS alone. Booster immunizations were performed at 14 (booster 1) and 28 (booster 2) days after the primary immunization. Serum was collected on the 4th day after challenge (35th day) for the serological analysis, and mouse survival was monitored on a daily basis for up to 53 days (Huang et al. (2011) "Modulation of immune responses by the antimicrobial peptide, epinecidin (Epi)-1, and establishment of an Epi-1-based inactivated vaccine" *Biomaterials* 32(14):3627-36, which is herein incorporated by reference in its entirety).

Statistical Analyses

Experiments were conducted in triplicate, and repeated three times. Univariate analysis of variance (ANOVA) in SPSS software (Chicago, Ill., USA) was used to analyze the significance among treatments. Error bars represent the standard deviation or standard error of the mean (SEM). The survival of tested animals was depicted using Kaplan-Meier curves and the corresponding analyses were performed by a log-rank test.

Results

Effects of Epi-1 Treatments in In Vitro Study

The effects of Epi-1 on JEV in BHK-21 cells were studied. In cell proliferation assays, cells treated with various concentrations of Epi up to 1 μg/ml for 48 h did not affect cell viability (n=3; data now shown). Then, overnight-cultured BHK-21 cells were infected with JEV at a multiplicity of infection (MOI) of 0.1 (equivalent to 5000 plaque-forming units (pfu)/well) with or without adding Epi-1. At 48 h, cell viability of JEV infection was determined (FIG. 1a). The pre- (prophylactic) and post-treatments (curative) with Epi-1 failed to prevent JEV infection. When cells were co-treated with 0.5 or 1 μg/ml Epi-1 plus JEV, infection rates dropped by 40% and 50%, respectively, compared to that of the control. Thus, Epi-1 should play a critical role in JEV inactivation in cells.

Epi-1 Performance on JEV Infection

In an animal study, mice (n=10) were first intraperitoneally (i.p.) injected with 200 μg/ml of Epi-1; all mice survived and behaved normally. No toxic effects were noted after Epi-1 inoculation. Epi-1 treatment against mice i.p.-injected with 50× the $LD_{50}$ of JEV ($1.5 \times 10^7$ pfu in 500 μl) was then performed. JEV was co-injected with or without Epi-1 at various dosages (50, 100, and 200 μg/ml) into adult mice and subsequently boosted (a second JEV challenge without Epi-1) on day 14. The survival rate of mice was recorded for 25 days. Without Epi-1 co-injection; all mice (n=10) died within 1 week; mice (n=10) that had received Epi-1 died only after JEV re-challenge (FIG. 1b). Ten mice that received JEV plus 200 μg/ml of Epi-1 surprisingly survived even after the second JEV re-challenge; they otherwise all behaved normally (FIG. 1b). Although one and four mice treated with JEV plus 100 and 50 μg/ml of Epi-1, respectively, died within 1 week, they behaved normally (n=10; FIG. 1b), was able to eat and move around actively like non-infected mice. An ideal dosage against JEV infection in this given model system may be 200 μg/ml of Epi-1. Co-injection of Epi-1 and JEV may induce some desirable adaptive immunity against JEV re-challenge.

Effects of Epi-1 on the Production of Neutralizing Antibodies

Figure 2:
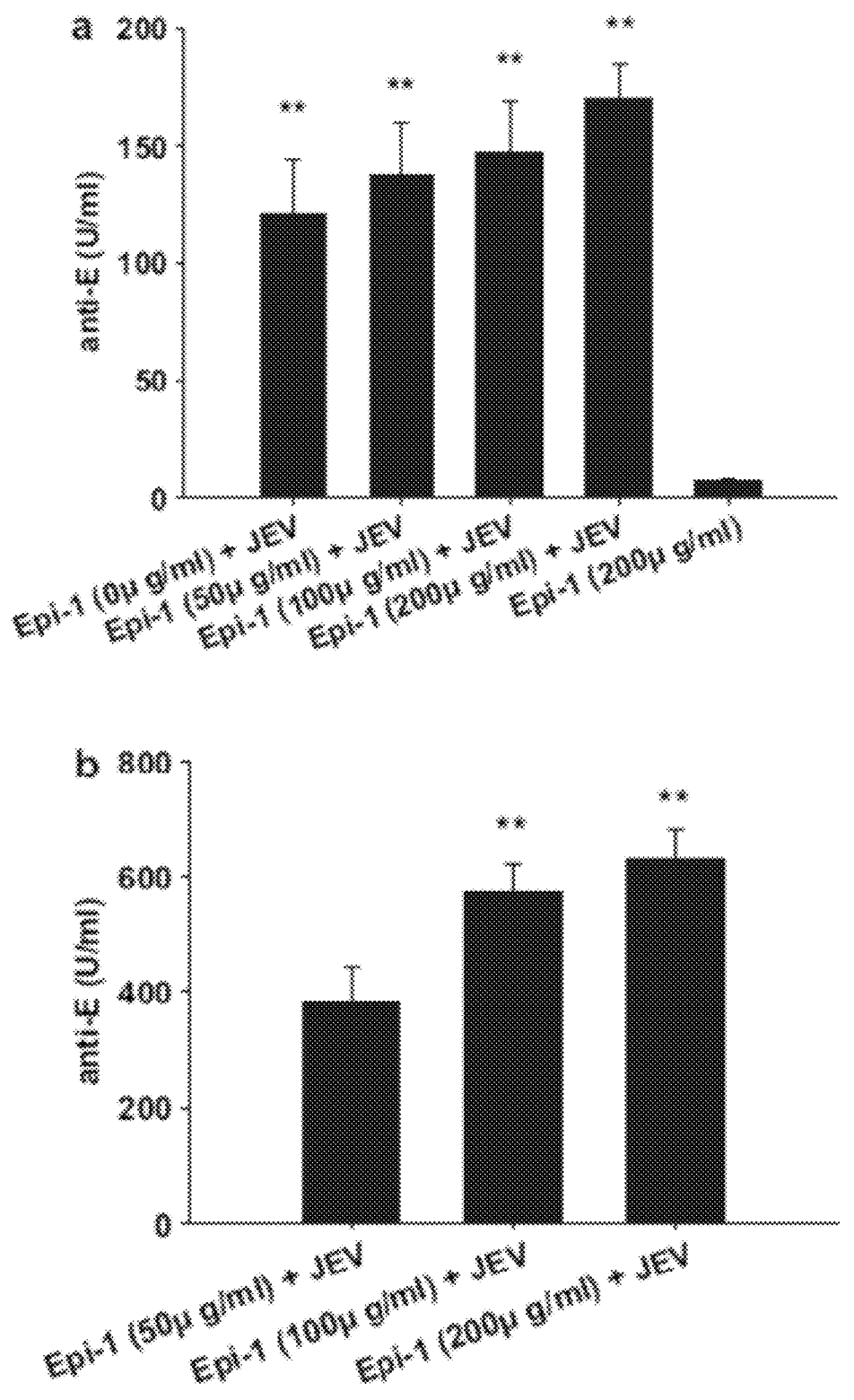
Figure 3:
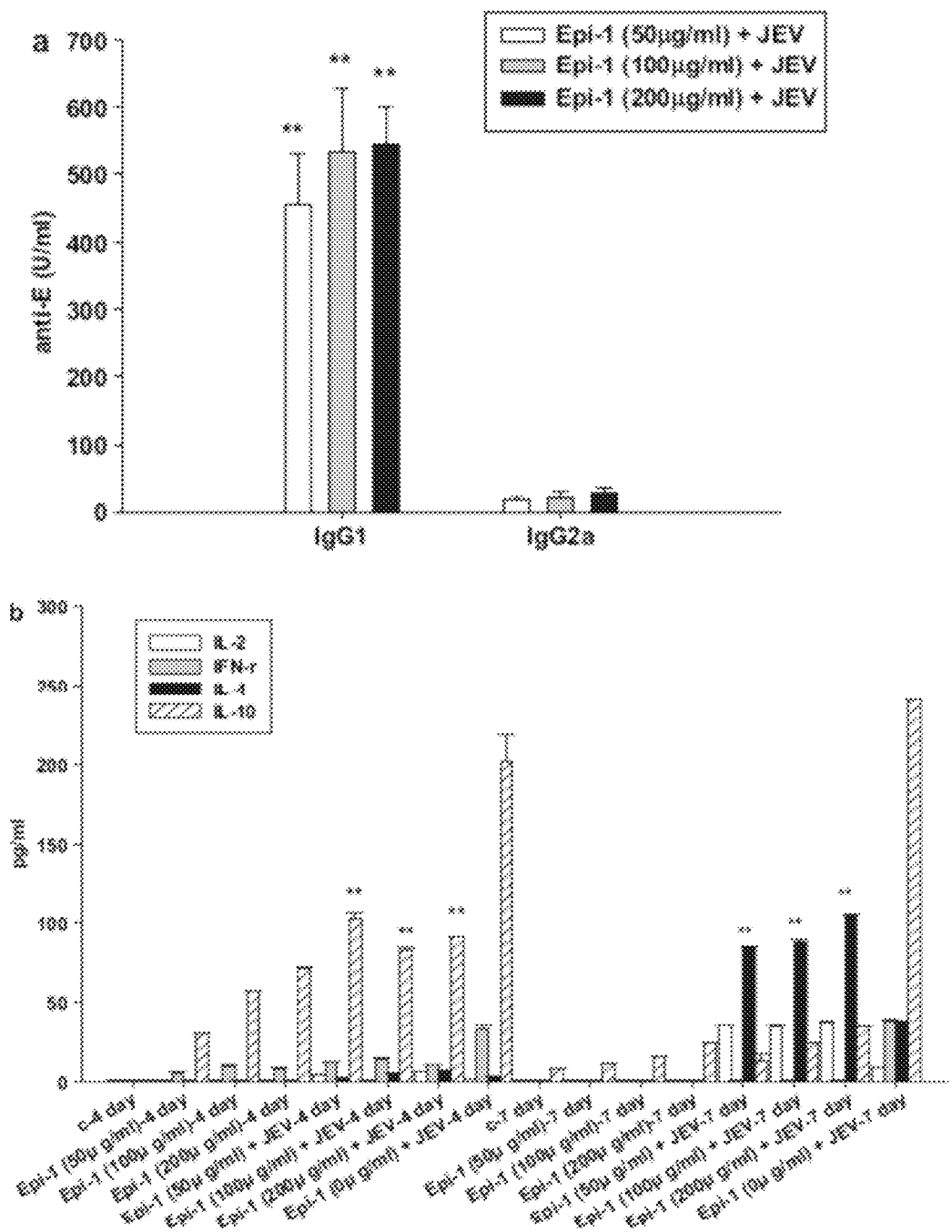
FIG. 3 shows Epinecidin (Epi)-1 preferentially activates immunoglobulin G1 (IgG1) and Th2 cytokines. Serum was collected at 4, 7 and 21 days after primary challenge and analyzed for the presence of Japanese encephalitis virus (JEV)-envelope (E) protein-specific IgG1 and IgG2a subclass antibodies (a) and cytokines (b) by an ELISA. The result was converted to relative units/ml against the control antibody. Sera collected from 50× the 50% lethal dose ($LD_{50}$) of JEV with 50 (E50), 100 (E100), and 200 (E200) μg/ml were included in the experiment. $*p<0.05$. Error bars, SEM. (n=4~7).

To evaluate whether co-injection of Epi-1 and JEV can induce neutralizing antibodies and serve as a vaccine against JEV infection, serum was collected on the 4th, 7th, and 21st days from surviving mice injected with 200 μg/ml of Epi-1, JEV, or JEV co-treated with different doses (50, 100, and 200 μg/ml) of Epi-1 and re-challenged JEV on the 14th day. The anti-JEV titer was determined and cytokine assays were performed using an enzyme-linked immunosorbent assay (ELISA). On the 4th day, mice co-injected with Epi-1 and JEV showed higher anti-JEV titers than JEV alone, and this further significantly increased after re-challenge (FIG. 2). The production of anti-JEV antibodies against JEV was through T-helper (Th) cells, $Th_1$ and/or $Th_2$. Co-injection of Epi-1 with JEV produced increased IgG1 antibodies, which suggests that Epi-1 activates $Th_2$ cells in response to JEV (FIG. 3). $Th_2$ cell activation resulting in the production of IgG1 is well documented as a humoral response. As shown in FIG. 3b, $Th_2$ cytokine levels (IL-4 and IL-10) were higher than $Th_1$ cytokine levels (IL-2 and INF-□) when Epi-1 was co-injected with JEV. Therefore, co-injection of Epi-1 and JEV can induce a humoral response against JEV infection.

Then, the anti-JEV neutralization ability of serum from C3H/HeN mice injected JEV with or without Epi-1 was examined by a plaque-reduction neutralization test. Sera were collected on the 7th day, and the JEV-E-neutralizing antibody titers were assayed. As shown in Table 1, no neutralizing antibody titer was detected (<1/10) in the group only treated with 0, 50, 100, and 200 μg/ml Epi-1. Surprisingly, a low neutralizing antibody titer was detected (<1/40) in the group treated with JEV alone. The group treated with JEV plus 200 μg/ml of Epi-1 showed the highest neutralizing antibody titer (>1/1280). The groups treated with JEV plus 50 and 100 μg/ml of Epi-1 respectively revealed >1/160 and >1/320 neutralizing antibody titers. These results showed that the co-injection of Epi-1 and JEV may be used as an inactivated vaccine, and it provided significant immune protection against JEV infection. Table 1 shows induction of neutralizing antibodies titers in mice co-injected with Epi-1 and JEV.

TABLE 1

| Mode[a] | Neutralizing antibodies titers[b] | |
|---|---|---|
| | −JEV | +JEV |
| Epi-1 (0 μg/ml) | <1/10 | <1/40 |
| Epi-1 (50 μg/ml) | <1/10 | >1/160 |
| Epi-1 (100 μg/ml) | <1/10 | >1/320 |
| Epi-1 (200 μg/ml) | <1/10 | >1/1280 |

[a]C3H/HeN mice were co-injected JEV with or without Epi-1 at various dosages (50, 100, and 200 μg/ml).
[b]JEV neutralizing antibodies titers in serum collected 7th day after treatment expressed as the reciprocals of the serum dilution yielding a 50% reduction in plaque numbers.

Effects of Epi-1 on the Expressions of JEV-Dependent Genes in Mice

To profile expressions of antiviral genes modulated by Epi-1 in JEV-infected mice, complementary (c)DNAs from brain sections of mice post-injected on days 4 or 14 were analyzed using a mouse 44 k oligo microarray. Genes expressed under [Epi-JEV] vs. [JEV] conditions were analyzed to understand the overall modulation of JEV-induced genes by Epi-1. Such immune-responsive, antiviral and inflammatory genes such as STAT1, STAT2, IL6, IFNB1, MyD88, MX1, TLR3, Casp4, TLR1, TLR7, IL7R, and IFNA5 were found to be regulated by Epi-1 (see Huang et al. (2011) "Modulation of immune responses by the antimicrobial peptide, epinecidin (Epi)-1, and establishment of an Epi-1-based inactivated vaccine" Biomaterials 32(14):3627-36 under the sections of "Supplementary data 1 and Supplementary FIG. 2"). In addition, genes associated with mitogen-activated protein kinase (MAPK) and calcium-dependent calmodulin kinase (CaMK) were also affected by Epi-1 in the microarray. The expression levels of given genes selected from those above were further investigated by real-time PCR. Table 2 shows a list of primers used for the real-time PCR analysis. cDNAs of mouse brain only injected with Epi-1 served as a control. Similar to the microarray results, expression levels of the genes, STAT1, STAT2, Bax, IFN-A7, IFN-β, IFN-γ, Mx-1, TLR-1, MyD88, IL-2, and Atf3, were down-regulated in mice injected with Epi-1 and JEV on day 4 (FIG. 4a, b). In contrast, the anti-apoptosis and anti-inflammatory genes, Bcl-2, SOCS-3, and IL-4, were upregulated (FIG. 4b). Since all mice infected with JEV died within a week, the expression levels of the given genes in mice co-injected with Epi-1 and JEV were compared to those of the control (the day 14 sample with Epi-1 treatment). Expressions of these given genes were generally low over 14 days (FIG. 4c, d). As a result, the expression levels of JEV immune-responsive and -induced antiviral genes were ascertained to have been down-regulated by Epi-1, which is consistent with the results of the microarray and quantitative PCR (FIG. 4c).

TABLE 2

| Gene | Sense | Antisense | PCR Product Size (bp) |
|---|---|---|---|
| Stat1 | tgtctagtgttatgagttggtt (SEQ ID NO: 2) | cttctggtgtccatacattca (SEQ ID NO: 3) | 137 |
| IL2 | tctgaggagatggatagc (SEQ ID NO: 4) | tgttgtaagcaggaggta (SEQ ID NO: 5) | 78 |
| Tlr1 | atgaaggctctgataact (SEQ ID NO: 6) | cttgtggtaattggtagg (SEQ ID NO: 7) | 77 |
| IL1f6 | tgttcaggatcttagtagt (SEQ ID NO: 8) | agcaaggtaatagtgact (SEQ ID NO: 9) | 99 |
| Ifnb1 | tacagggcggacttcaag (SEQ ID NO: 10) | ctcattccacccagtgct (SEQ ID:NO: 11) | 138 |
| Gapdh | acaatgaatacggctacag (SEQ ID NO: 12) | ggtccagggtttcttact (SEQ ID NO: 13) | 78 |
| Stat2 | aaggcacaacagcatagt (SEQ ID NO: 14) | agatggtacagcagagaac (SEQ ID NO: 15) | 86 |
| Nfkb1 | atttgctttgtgttgtta (SEQ ID NO: 16) | ttacagtagatggctaga (SEQ ID NO: 17) | 101 |
| Ifna7 | cttcctcagactcataac (SEQ ID NO: 18) | atctaaagtcctttctgtc (SEQ ID NO: 19) | 106 |
| Myd88 | ttcactgcttgatgttga (SEQ ID NO: 20) | gcccttcttttctttattga (SEQ ID NO: 21) | 104 |
| Ifng | cacacctgattactaccttct (SEQ ID NO: 22) | cctcaaacttggcaatactc (SEQ ID NO: 23) | 75 |
| IL4 | ttagcatctcttgataaacttaa (SEQ ID NO: 24) | aaatgccgatgatctctc (SEQ ID NO: 25) | 165 |
| IL7r | gaccttgctacacatcttcag (SEQ ID NO: 26) | attcaccacatccttctatcttc (SEQ ID NO: 27) | 198 |
| Mx1 | cctgccatcgctgtcattg (SEQ ID NO: 28) | tgcctctccactcctctcc (SEQ ID NO: 29) | 157 |

Effects of Epi-1 on the JEV-Associated Proinflammatory Cytokines

Figure 4:
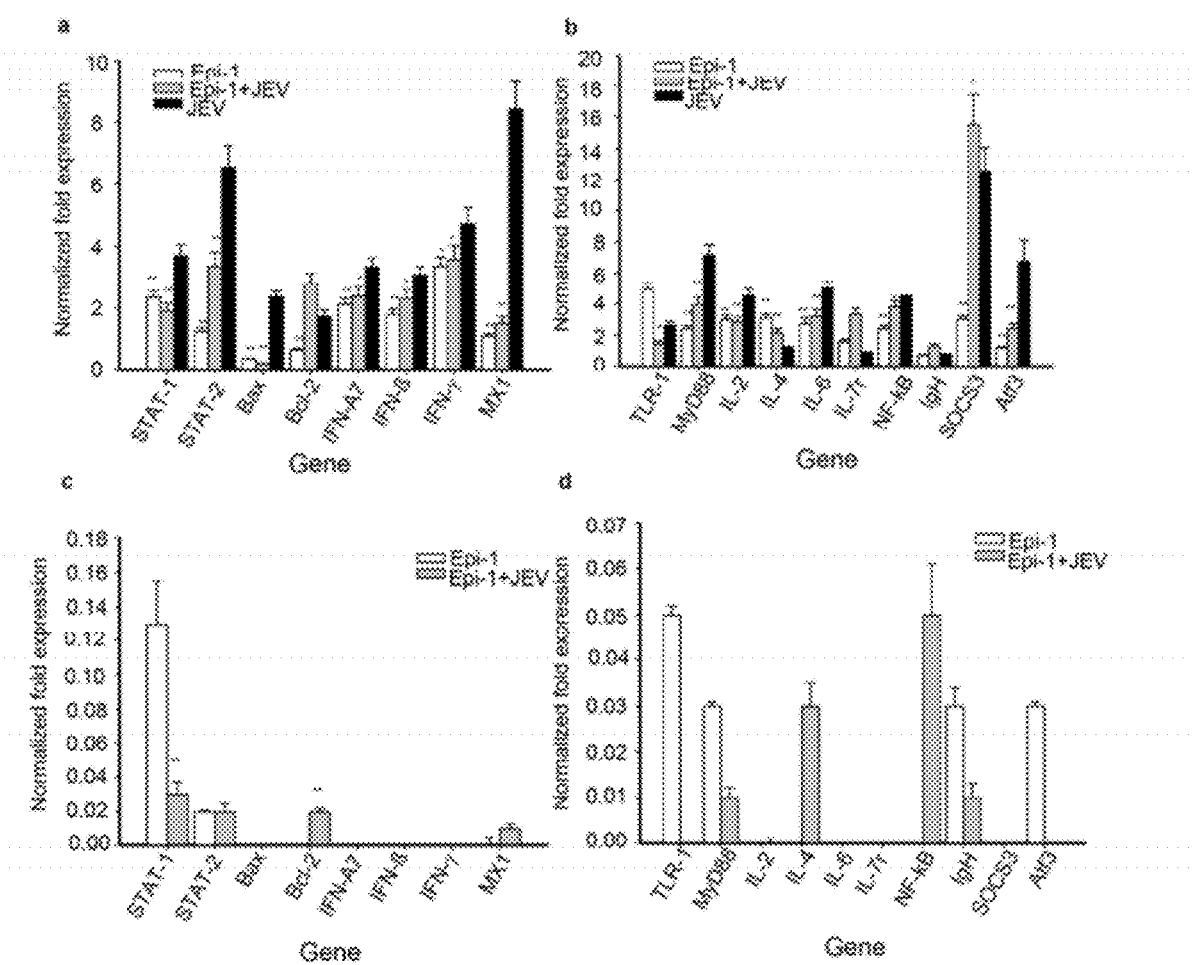
FIG. 4 shows the expression patterns of selective anti-viral and immune response genes in epinecidin (Epi)-1 and/or Japanese encephalitis virus (JEV)-injected mice at 4 and 14 days. Mice were i.p. injected with 50× the 50% lethal dose ($LD_{50}$) of JEV in the presence or absence of 200 μg/ml Epi-1 (Epi-1+JEV and JEV respectively) or 200 μg/ml Epi-1 alone (Epi-1), and cDNA isolated from the brain at 4 and 14 days post-injection and JEV-responsive gene expressions in the presence of Epi-1 were detected by a real-time PCR analysis. Gene expressions were normalized to GAPDH, and converted to multiples of change over the untreated control. $*p<0.05$. Error bars, s.d. (n=3).
Figure 5:
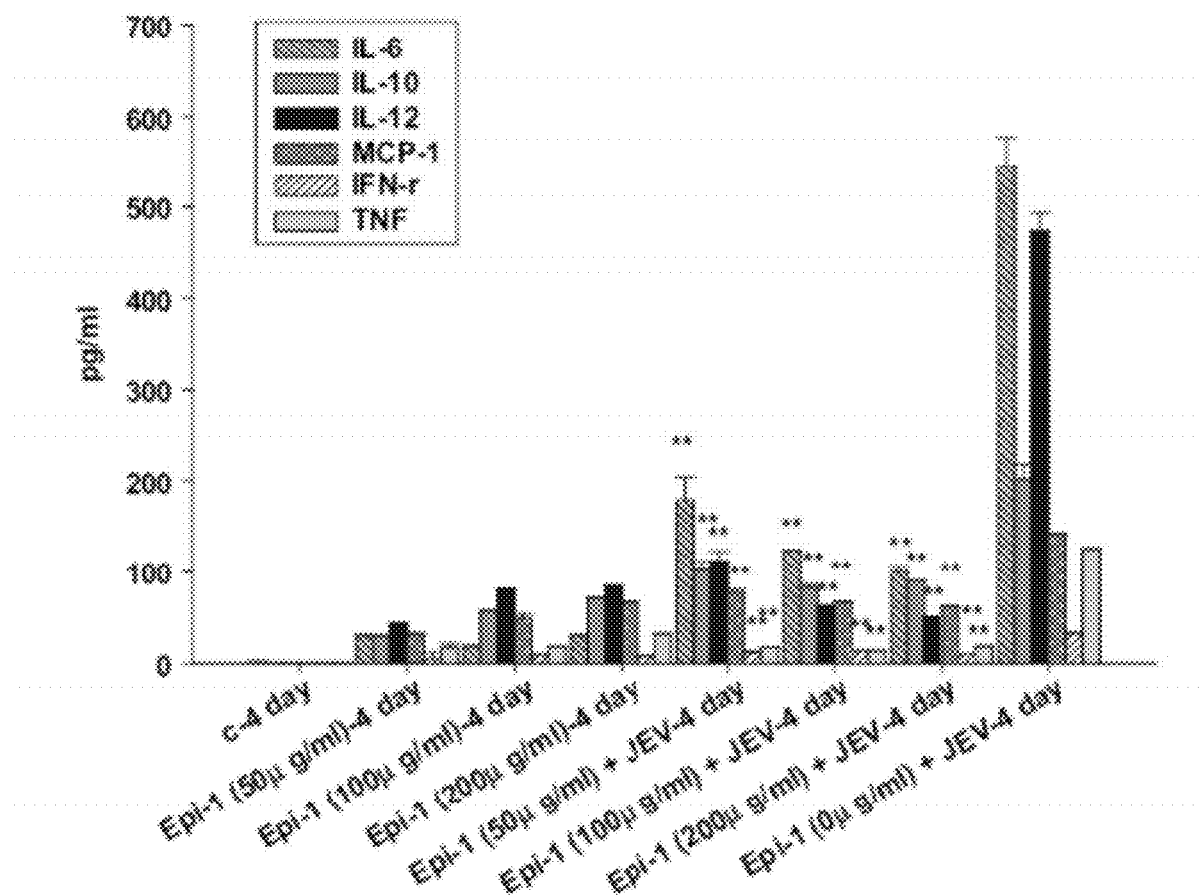
FIG. 5 shows Epinecidin (Epi)-1 regulates proinflammatory cytokines. Mice were i.p. injected with the Japanese encephalitis virus (JEV), Epi-1, and JEV with Epi-1 at 50 (E50), 100 (E100) and 200 (E200) μg/ml. and selective proinflammatory cytokines in the brain were measured by a cytokine ELISA at 4 days post-treatment. (n=3).

To understand the effects of Epi-1 on proinflammatory cytokine release in mice infected by JEV, we measured levels of IL-6, IL-10, IL-12p70 MCP-1, TNF, and IFN-γ from 4-day-treated samples using a BD OptEIA™ with an ELISA kit (BD Bioscience, San Diego, Calif., USA). The JEV-mediated release of IL-6, IL-10, IL-12p70, MCP-1, TNF, and IFN-γ was found to be suppressed by Epi-1 (FIG. 5), as manifested in gene and protein expression levels (FIG. 4).

Epi-1 Performance on JEV-Infected Mouse Brain

Next, we studied whether Epi-1 directly acts as an antiviral agent against JEV. JEV mixed with 50, 100, or 200 μg/ml of Epi-1 for 15 min at room temperature (RT) was fixed on a slide for transmission electron microscopic (TEM) inspection. Viral particles were found to be subject to lysis and destruction in the presence of Epi-1 (Supplementary FIG. 3). To study the in vivo antiviral activities, adult mice were injected with either 50× the 50% lethal dose ($LD_{50}$) of JEV alone or JEV and Epi-1 (50, 100, or 200 μg/ml). On day 4 after treatment, brain specimens were treated first with an anti-JEV-E primary antibody and then a goat anti-mouse-conjugated FITC secondary antibody. Samples were then subjected to a fluorescence microscopic examination (with an FITC filter). Bright fluorescent dots, representing virus particles associated with anti-JEV-E, were clearly observed in the JEV-alone samples, but the numbers of spots dramatically decreased in samples co-injected with Epi-1 and JEV (FIG. 6a). Total proteins from brain samples were further subjected to a Western blot analysis, using an anti-JEV-E antibody (FIG. 6b). The 52-kDa JEV-E protein was clearly noted in mice samples injected with JEV, while it was barely seen in samples with Epi-1. Differences in relative intensities were up to 6-fold between samples co-injected with Epi-1 (200 μg) and those injected with JEV alone (FIG. 6c). These results show that Epi-1 directly acts as an antiviral agent against JEV infection.

The Effects of Epi-1-Inactivated Vaccine on Neonate Mice

Figure 7:
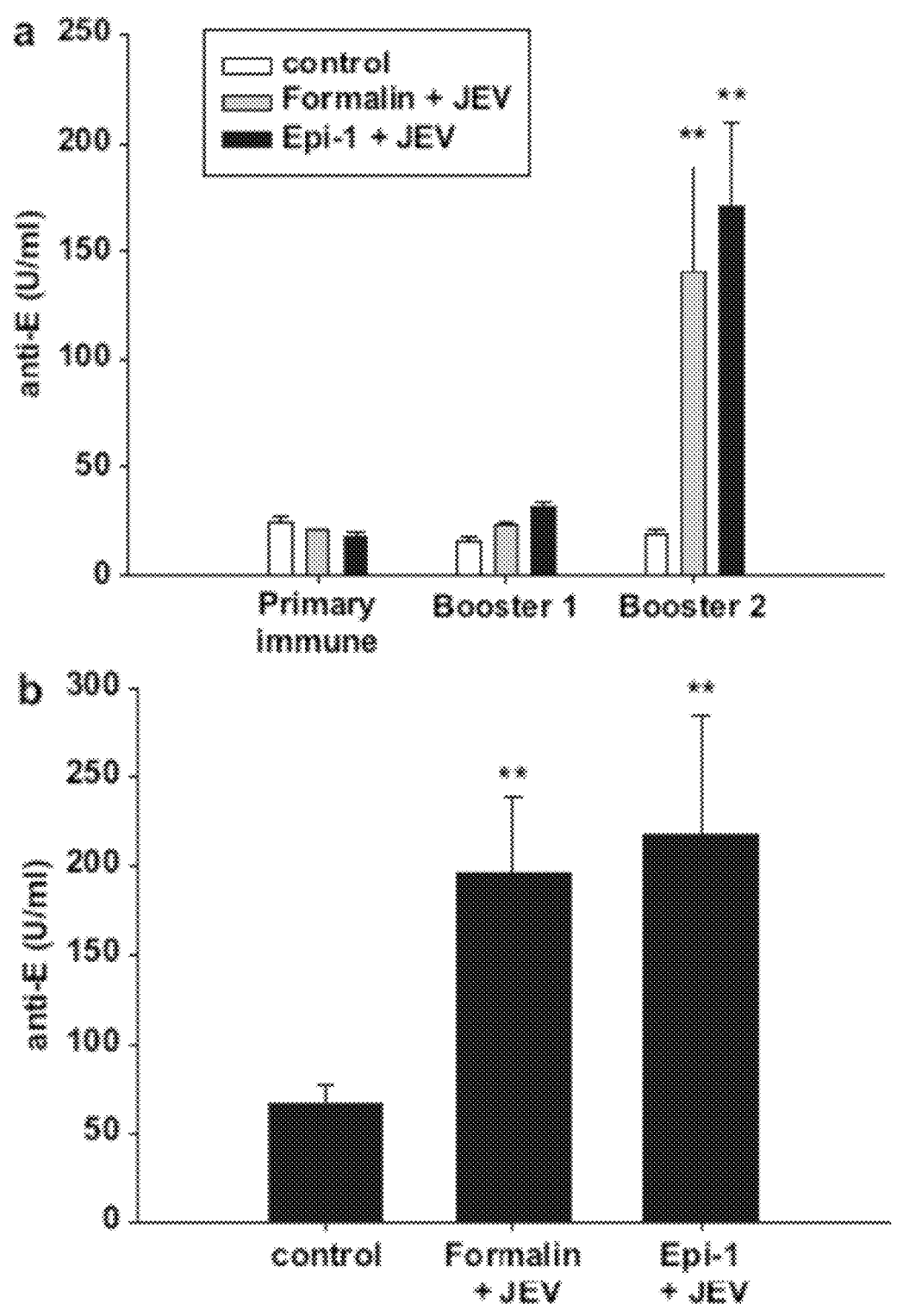
Figure 8:
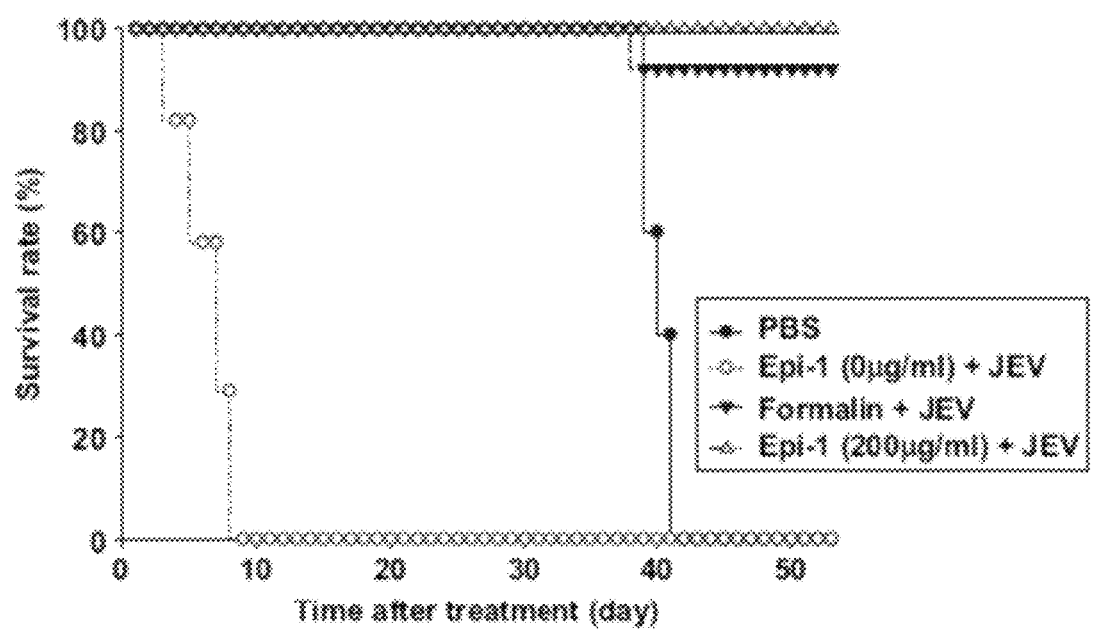
FIG. 8 shows epinecidin (Epi)-1-based Japanese encephalitis virus (JEV)-inactivated vaccine enabled complete immunity of the neonate mice against JEV infection. C3H/HeN neonate mice received three immunizations with formaldehyde-JEV- or Epi-1-JEV-inactivated vaccines at 7, 14, and 28 days of age. Only PBS was applied to control mice. On the 35th day, all mice were infected with 50× the 50% lethal dose ($LD_{50}$) of JEV, and survival was monitored on a daily basis. (n=10~13).

Mouse brain-derived, formalin-killed vaccines are currently used in countries with vaccine-preventable infections, including Taiwan. The limitations of formalin-inactivated JE vaccines include the high cost of manufacture, a lack of long-term immunity, the need for multiple doses, and the risk of allergic reactions. To determine whether Epi-1-inactivated JEV can serve as a vaccine in neonate mice, we formulated a solution of Epi-1 (200 μg/ml) plus 50× the $LD_{50}$ of JEV ($1.5 \times 10^7$ pfu). In parallel, a formalin-inactivated JEV vaccine was prepared according to standard procedures to serve as a positive control. A primary immunization was performed in 7-day-old neonate mice; boosters were given on days 14 and 28. Anti-JEV antibodies were then measured by an ELISA. The anti-JEV-E titer activity was poor after the primary immunization in both tested groups (FIG. 8a). After the second immunization, the anti-JEV-E titers significantly increased in mice vaccinated with either vaccine but the group with Epi-1 was slightly higher. After the third immunization, levels of the anti-JEV-E antibody were determined to be about 150 units in serum of vaccinated mice, but again that of the group with Epi-1 was slightly higher (FIG. 7a). With JEV challenge, the anti-JEV-E titers dramatically increased to 200 units on day 4 in both vaccinated groups, while the group with Epi-1 was higher (FIG. 7b). On the other hand, the survival rates of mice re-challenged with 50× the $LD_{50}$ of JEV on the 35th day showed the following results: all Epi-1-JEV-immunized mice (n=13) survived (FIG. 8); all but one of the formalin-JEV-immunized mice survived, as opposed to all controls that died within 1 week. As a result, the Epi-1-based JEV-inactivated vaccine performed the same as or slightly better than the conventional vaccine in preventing JEV infection in neonate mice.

Discussion

The antiviral and host defense functions of Epi-1 against JEV infection were determined both in vitro and in vivo, so that Epi-1 is an antiviral against JEV and is able to modulate some immune-related genes in the mouse. Epi-1 showed no detectable cytotoxicity toward BHK-21 cells or in adult mice, although several AMPs were reported to be cytotoxic at high levels. In addition, Epi-1 was not reported to exhibit any cytotoxicity in previous reports. This information suggests that Epi-1 acts as a host-friendly peptide and can be used for advanced studies.

In vivo studies demonstrated that 200 μg/ml of Epi-1 is an appropriate quantity to achieve desired immune responses. The induction of IgG1 was correlated with activation of $Th_2$ cells as well as a humoral immune response in the given conditions. The increased production of the anti-E-neutralizing antibody in Epi-1/JEV-co-treated mice was ascribed to an induction of adaptive immunity (FIGS. 2, 3; Table 1). Epi-1/JEV-co-treated mice induced higher $Th_2$ cytokine levels (IL-4 and IL-10) than $Th_1$ cytokine levels (IL-2 and INF-γ). The antibody isotyping revealed that the induction of IgG1 by Epi-1 was through $Th_2$ cells, so it was a humoral response (FIG. 3). In FIG. 4, the IL-7 receptor (IL7R) plays a critical $Th_2$ role in V(D)J recombination during lymphocyte development which was also activated.

The microarray and real-time PCR confirmed that Epi-1 modulates gene expressions during JEV infection (FIG. 4). In Epi-1/JEV-co-treated mice, virus-induced STAT1 and STAT2 were down-regulated, then the expressions of downstream genes were reduced, including IFN-A7, IFN-β, and IFN-γ (FIG. 4). IFN-γ is normally induced by $Th_1$ cells, but $Th_1$ cells were not induced by Epi-1, which is consistent with our observations. JEV can induce caspase-3 activation of mitochondrion-mediated apoptosis and increase inflammatory cytokine secretion. Interestingly, co-injection of Epi-1 with JEV induced Bcl-2 but suppressed Bax-2 expression (FIG. 4), so that Epi-1 possesses pro-survival and proapoptotic functions. The Mx protein is responsible for a specific antiviral state against virus infection. Activation of Mx-1 was also mediated by Epi-1. Therefore, Epi-1 may prevent JEV-induced-host defense mechanism-mediated cell death by directly damaging viral particles. Toll-like receptor (TLR) 1 is a member of the TLR family of pattern-recognition receptors of the innate immune system, and its downstream adapter, MyD88, can activate the transcription factor, NF-κB, to stimuli cytokines (such as IL-2 and IL-6 which are involved in the activation of macrophages, and B and T cells). However, these genes were down-regulated on day 4 in mice injected with Epi-1 and JEV (FIG. 4b). Atf3 prevents immune pathologies associated with uncontrolled proinflammatory cytokine production. The down-regulation of proinflammatory cytokines such as TNF-α, IL-12, IL-6, and MCP-1 by Epi-1 (FIG. 5) may prevent an autoimmune disorder from uncontrolled induction of these cytokines. The expression profiles of major immune-responsive genes (FIG. 4) in the study were in agreement with this inference.

Figure 6:
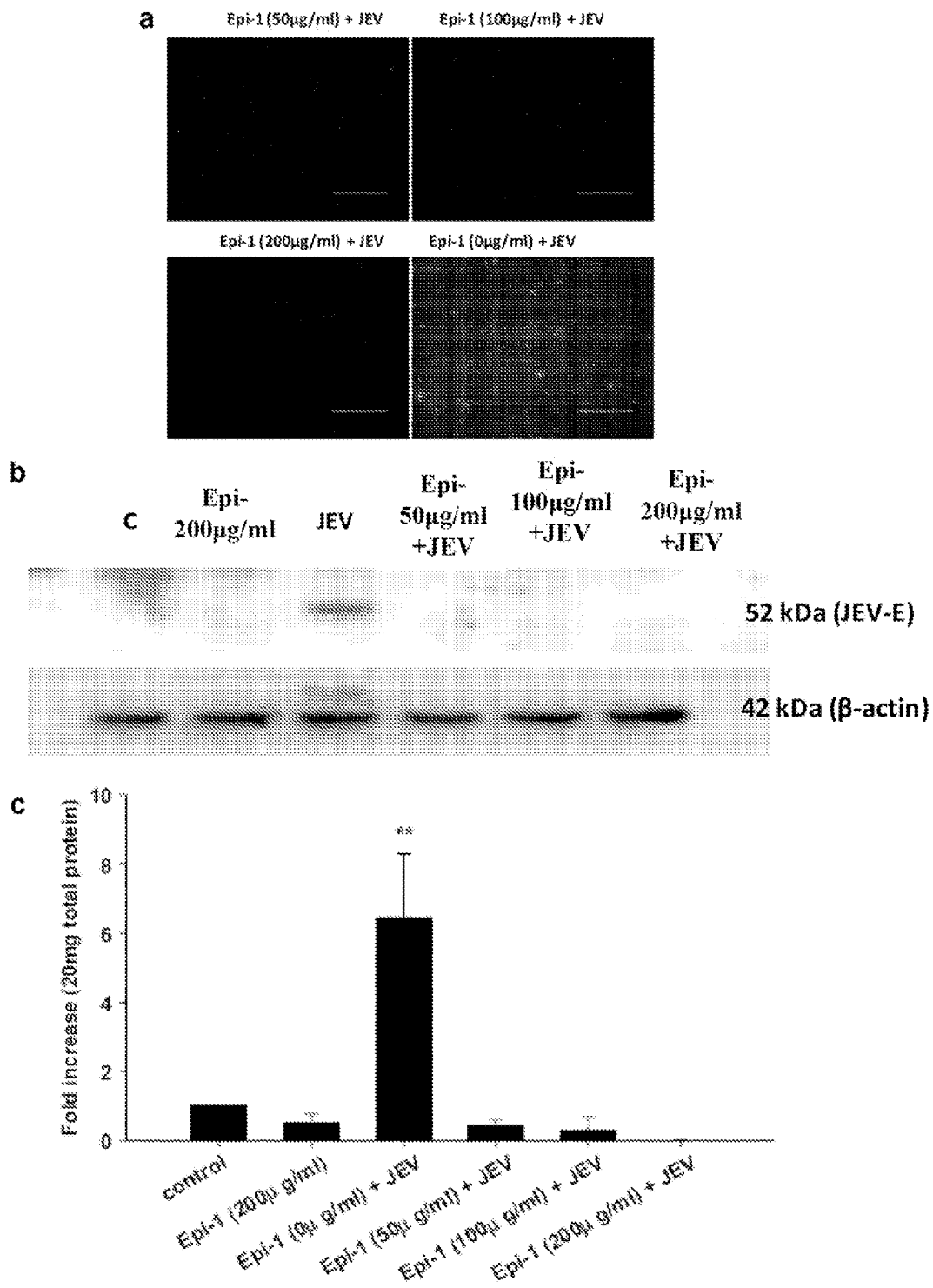
FIG. 6 shows Epinecidin (Epi)-1 controls Japanese encephalitis virus (JEV) multiplication in the mouse brain. (a) Processed brain sections from 4-day post-treated mice were incubated with a primary anti-JEV-envelope (E) protein antibody and a secondary goat anti-mouse-conjugated FITC antibody. Samples were visualized under a fluorescence microscope using an FITC filter. (b) Total proteins from brain samples of mice injected with 10 μg from control (C), 50× the 50% lethal dose ($LD_{50}$) of JEV, and JEV with Epi-1 at 50 (E50), 100 (E100), and 200 (E200) μg/ml were subjected to a Western blot analysis using an anti-JEV-E primary antibody. (c) The intensity of the JEV-E protein expression in Western blots was measured by a densitometer and normalized to the untreated control (C). $*p<0.05$. Error bars, s.d. (n=3).

The immunofluorescence experiments and Western blot analysis demonstrated that Epi-1 has an antiviral function (FIG. 6). Electron microscopic examination provided further support that Epi-1 directly interacts with JEV (See Huang et al. (2011) "Modulation of immune responses by the antimicrobial peptide, epinecidin (Epi)-1, and establishment of an Epi-1-based inactivated vaccine" Biomaterials 32(14):3627-

36 under the sections of "Supplementary FIG. 2"). The idea of using Epi-1 to develop a JEV-inactivated vaccine therefore is workable.

The much-increased anti-E antibody demonstrated that an Epi-1-based vaccine was superior to the traditional formalin-inactivated vaccine. Previous studies showed that the clinical efficiency of a formalin-based inactivated vaccine was around 91%, while the Epi-1-inactivated JEV vaccine-immunized mice reached 100% survival in this study. We consider Epi-1 to be very promising as a substitute for formalin in vaccine development, although additional clinical studies are required for its subsequent development. Nevertheless, the new use of Epi-1 demonstrated herein should pave the way for the next generation of JEV vaccines.

CONCLUSIONS

In this study, an antimicrobial peptide of epinecidin-1 (Epi-1) was synthesized and evaluated for an Epi-1 based inactivated vaccine with Japanese encephalitis virus (JEV) by in vitro and in vivo assays was as an example. The Epi-1 has an antiviral function and inhibited Japanese encephalitis virus (JEV) activity by a co-treatment method in which it functioned as an inactivated vaccine. Epi-1 modulated the expressions of immune-responsive genes like interleukin (IL)-6, IL-10, MCP-1, tumor necrosis factor-$\alpha$, interferon-$\gamma$ and IL-12, and elevated the levels of anti-JEV-neutralizing antibodies in the serum. The ability of these two types of adjuvants of formalin and Epi-1 to protect neonate mice by immunization with inactivated vaccines in the in vivo test suggested that the approach of using Epi-1 for vaccine modification is a promising strategy and could replace the role of formalin. In particular, addition of Epi-1 features to other virus presents excellent opportunities in the development of new vaccines as well as applications in general.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method of enhancing a mammalian immune response to a virus, comprising:
    administering a composition comprising an effective amount of epinecidin (Epi)-1 and the virus to a mammal in need thereof, and thereby enhancing the mammal's immune responses against the virus, wherein the virus has envelope protein and is infectious to the mammal.

2. The method of claim 1, further comprising causing enhanced production of anti-envelope protein antibody in the mammal.

3. The method of claim 1, further comprising causing enhanced activation of T-helper cells in the mammal.

4. The method of claim 3, further comprising causing enhanced secretion of IL-4 in the mammal.

5. The method of claim 1, wherein the virus comprises a Japanese encephalitis virus (JEV).

6. The method of claim 1, wherein the composition induces neutralizing antibody titer against JEV in the mammal and the neutralizing antibody induction is epinecidin-1 dose-dependent.

7. The method of claim 1, further comprising causing enhanced production of neutralizing antibody against the virus in the mammal.

8. The method of claim 1, further comprising:
    causing enhanced expression of an immune-responsive gene, wherein the immune-responsive gene is chosen from B-cell CLL/lymphoma 2 (Bcl-2), interleukin 4 (IL-4) and suppressor of cytokine signaling 3 (SOCS3).

9. The method of claim 1, wherein the administering step is performed at least 3 times at a specified time interval.

10. The method of claim 5, wherein the administering step is performed at least 3 times at a specified time interval.

11. The method of claim 5, which reduces risk of death to the mammal during a challenge by the virus.

12. The method of claim 5, which increases survival of the mammal during a challenge by the virus.

13. A method of enhancing a mammalian immune response to a virus, comprising:
    co-administering an effective amount of Epi and the virus to a mammal in need thereof, and thereby enhancing the mammal's immune response against the virus, wherein the virus has envelope protein and is infectious to the mammal.

14. The method of claim 13, wherein the co-administering step is performed at least 3 times at a specified time interval.

15. The method of claim 14, wherein the virus comprises a Japanese encephalitis virus (JEV).

16. The method of claim 15, which increases survival of the mammal during a challenge by the virus.

17. A method of enhancing an animal's immune response to an infectious virus, comprising:
    administering a composition comprising an effective amount of epinecidin (Epi)-1 and the infectious virus to an animal in need thereof, and thereby enhancing the animal's immune response against the virus, wherein the virus is not a nervous necrosis virus.

18. A kit comprising:
    (a) a composition comprising an effective amount of epinecidin (Epi)-1 and a Japanese encephalitis virus (JEV); and
    (b) an insert containing, instructions on a method of enhancing a mammalian immune response to Japanese encephalitis virus (JEV) according to claim 11.

19. A kit comprising:
    (a) a composition comprising an effective amount of epinecidin (Epi)-1 and a Japanese encephalitis virus (JEV); and
    (c) an insert containing instructions on a method of enhancing a mammalian immune response to Japanese encephalitis virus (JEV) according to claim 16.

* * * * *